United States Patent [19]
Ichihara et al.

[11] Patent Number: 5,457,321
[45] Date of Patent: Oct. 10, 1995

[54] SPECT APPARATUS UTILIZING FAN-PARALLEL DATA CONVERSION

[75] Inventors: Takashi Ichihara, Ootawara; Akiyoshi Kinda, Urawa, both of Japan

[73] Assignee: Kabushiki Kaisha Toshiba, Kawasaki, Japan

[21] Appl. No.: 237,421

[22] Filed: May 3, 1994

Related U.S. Application Data

[63] Continuation of Ser. No. 658,204, Feb. 20, 1991, abandoned.

[30] Foreign Application Priority Data

Feb. 20, 1990 [JP] Japan .................................. 2-38576
Sep. 11, 1990 [JP] Japan .................................. 2-241005

[51] Int. Cl.⁶ .................................................. G01T 1/166
[52] U.S. Cl. .................... 250/363.04; 378/901; 250/369
[58] Field of Search .......................... 128/653.1; 378/901, 378/14, 18, 19; 382/6; 364/413.13, 413.14, 413.16, 413.17, 413.18, 413.19

[56] References Cited

U.S. PATENT DOCUMENTS

| | | | |
|---|---|---|---|
| 4,097,744 | 6/1978 | LeMay | 378/14 |
| 4,138,611 | 2/1979 | Hounsfield | 378/18 |
| 4,160,911 | 7/1979 | Hounsfield | 378/19 |
| 4,472,823 | 9/1984 | Waltham | 364/413.17 |
| 4,549,265 | 10/1985 | Deckers et al. | 364/413.16 |
| 4,703,424 | 10/1987 | Gullberg et al. | 364/413.21 |
| 4,812,983 | 3/1989 | Gullberg et al. | 378/901 |
| 4,973,913 | 11/1990 | Oda | 250/369 |
| 4,979,111 | 12/1990 | Nishimura | 364/413.18 |
| 5,128,864 | 7/1992 | Waggener et al. | 364/413.2 |
| 5,136,165 | 8/1992 | Lumma | 250/369 |
| 5,173,852 | 12/1992 | Lonn | 364/413.14 |
| 5,253,171 | 10/1993 | Hsiao et al. | 364/413.19 |
| 5,262,946 | 11/1993 | Heuscher | 364/413.18 |

OTHER PUBLICATIONS

Kruger et al., "Industrial Applications of computed tomography at Los Alamos Scientific Laboratory", May/Jun. 1980, pp. 273–282.

*Primary Examiner*—Gail O. Hayes
*Assistant Examiner*—Jennifer Hazard
*Attorney, Agent, or Firm*—Oblon, Spivak, McClelland, Maier & Neustadt

[57] ABSTRACT

A SPECT apparatus for forming a radioisotope distribution topographic image of an object, in which a detector such as a fan beam collomator detects fan beam shaped gamma ray emitted from a radioisotope given to the object to provide fan beam data, while a scanner causes relative rotation between the object and the detector, and a data collector collects the fan beam data, and in which a data converter successively converts the fan beam data into parallel beam data during the relative rotation, and a reconstructor reconstructs a tomographic image from the parallel beam data. The fan beam data having a first matrix size and a first angle may be converted into the parallel beam data having a second matrix size and a second angle which are different from the first matrix size and the first angle, respectively.

10 Claims, 13 Drawing Sheets

FIG.1
PRIOR ART

γ-RAY

FIG.2
PRIOR ART

γ-RAY

FIG.15 i FRAME       i+1 FRAME

SPECT APPARATUS UTILIZING FAN-PARALLEL DATA CONVERSION

This application is a continuation of application Ser. No. 07/658,204, filed on Feb. 20, 1991, now abandoned.

BACKGROUND OF THE INVENTION

1. Field of the Invention

The present invention relates to a SPECT (Single-Photon Emission Computed Tomography) apparatus for detecting gamma rays emitted from an RI (radioisotope) given to an object by a detector such as a gamma camera to obtain detection data and reconstructing an image using the detection data to obtain a density distribution tomographic image of the RI in the object, and more particularly to a fan beam SPECT apparatus for obtaining the detection data by using a fan beam collimator.

2. Description of the Background Art

Figure 1:
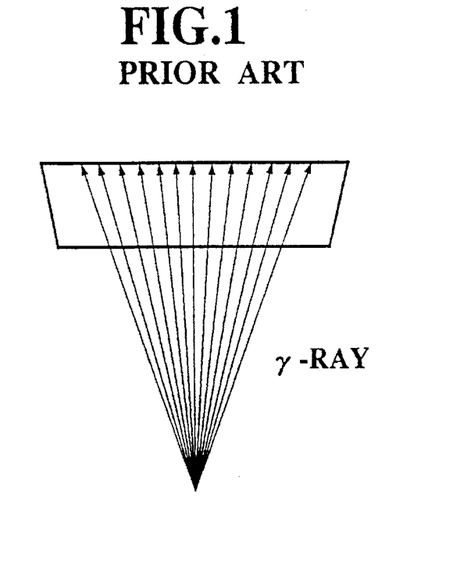
FIG. 1 schematically shows a conventional fan beam collimator.
Figure 2:
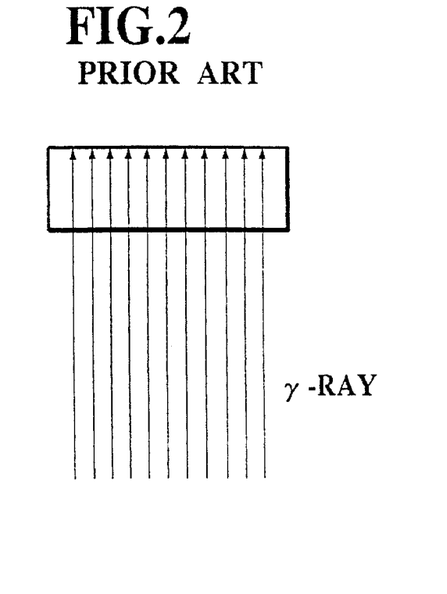
FIG. 2 schematically shows a conventional parallel beam collimator.
Figure 3:
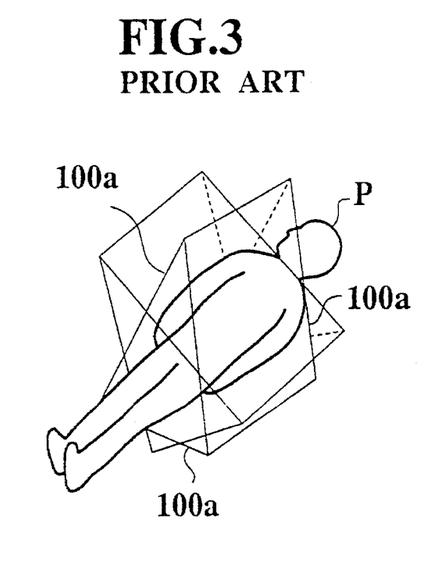
FIGS. 3 and 4 schematically show gamma ray incidence surfaces of conventional fan beam collimators during photographing an object.
Figure 4:
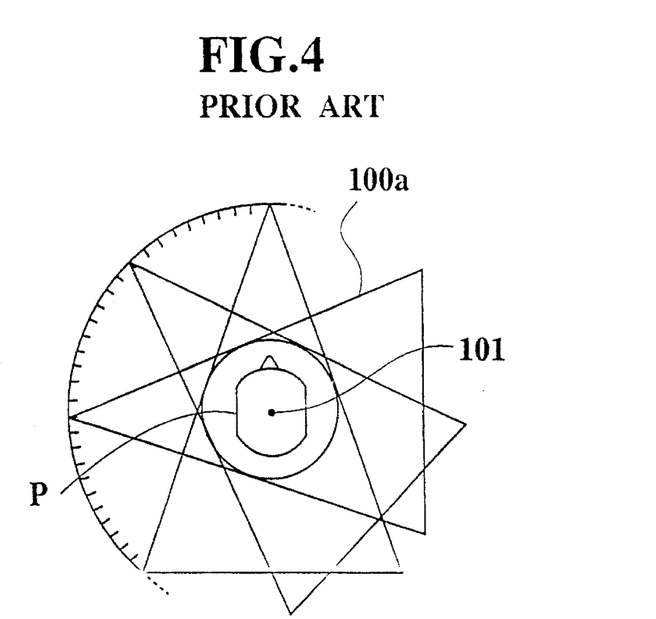

As shown in FIGS. 1 and 2, in a conventional SPECT apparatus of this kind, gamma rays are detected by a fan beam collimator or a parallel beam collimator. When the fan beam collimator is used, the gamma rays emitted from an RI (radioisotope) administered within an object can be effectively and advantageously detected. For example, three fan beam collimators are arranged, as shown in FIGS. 3 and 4, gamma ray incidence surfaces 100a of the fan beam collimators are rotated around an object P such as a man to detect the gamma rays emitted by the RI given to the object over a range of 360 degrees. In FIG. 4, 101 denotes a rotation center of the fan beam collimators.

In order to reconstruct an image from fan beam data detected by the fan beam collimators, the fan beam data is converted into parallel beam data which is the same data as that detected by using parallel beam collimators (fan-parallel data conversion), and the image is reconstructed using the parallel beam data in a parallel beam data reconstruction system. Alternatively, an image can be reconstructed using the fan beam data detected by the fan beam collimators in a fan beam data reconstruction system.

Figure 5:
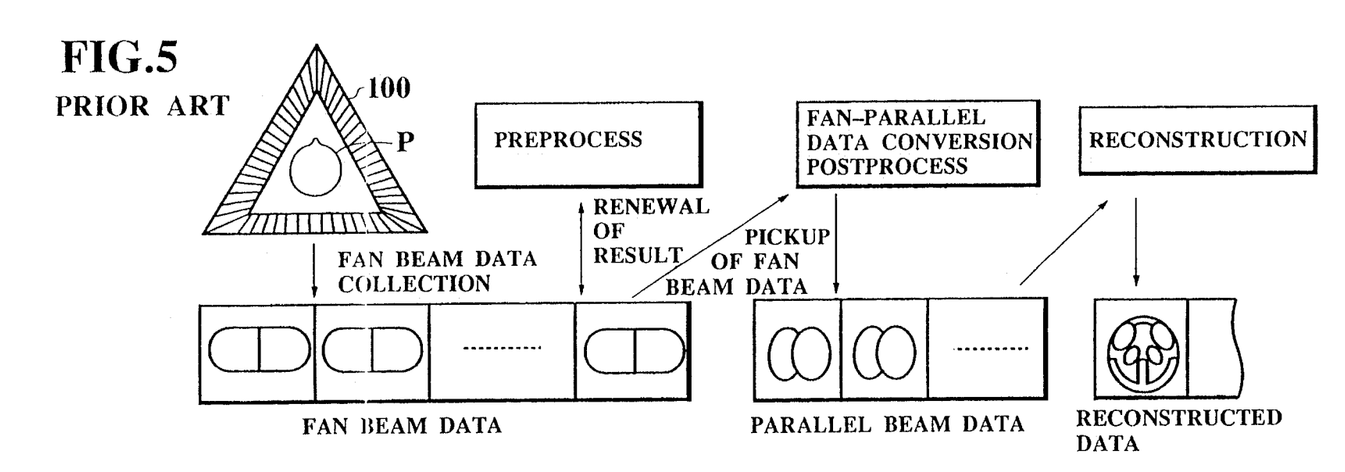
FIGS. 5 and 6 schematically show image reconstruction argorisms used in a conventional fan beam data collection SPECT apparatus.
Figure 6:
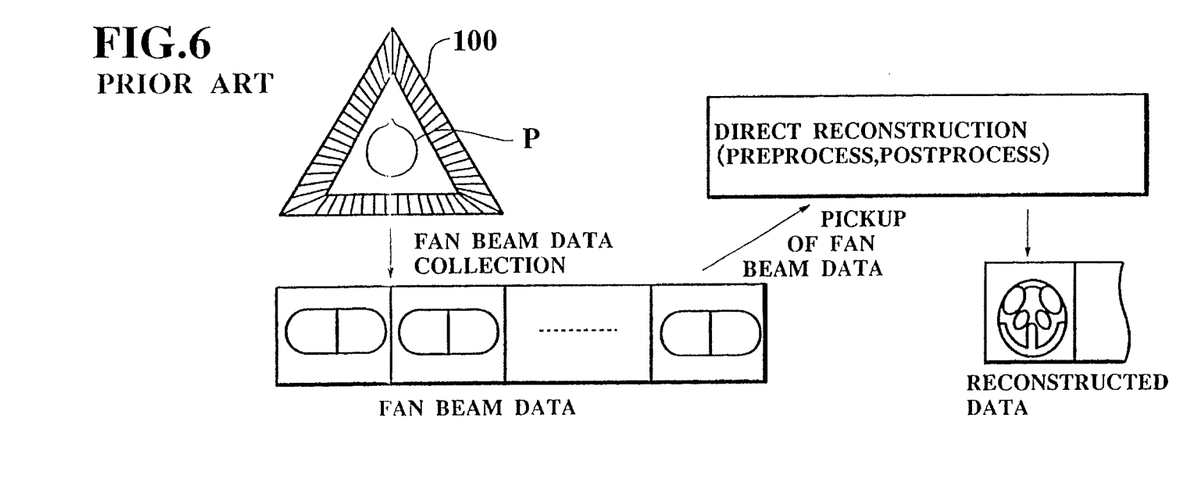

In the former case, as shown in FIG. 5, the gamma rays emitted the object P are detected by using three fan beam collimators 100 arranged in a triangular form to obtain fan beam data, and after collecting all of the fan beam data, if necessary, a preprocess such as a uniformity correction, a central position correction, a space filter process or the like is carried out. Then, the preprocessed fan beam data is picked up, and a fan-parallel data conversion and a post-process are carried out to obtain the parallel beam data. The image is reconstructed using the parallel beam data to obtain a density distribution tomographic image of the RI in the object. In the latter case, as shown in FIG. 6, the fan beam data detected by the fan beam collimators 100 are picked up and after, if necessary, carrying out the preprocess, the image is reconstructed according to a direct reconstruction algorithm to obtain reconstructed data.

Figure 7:
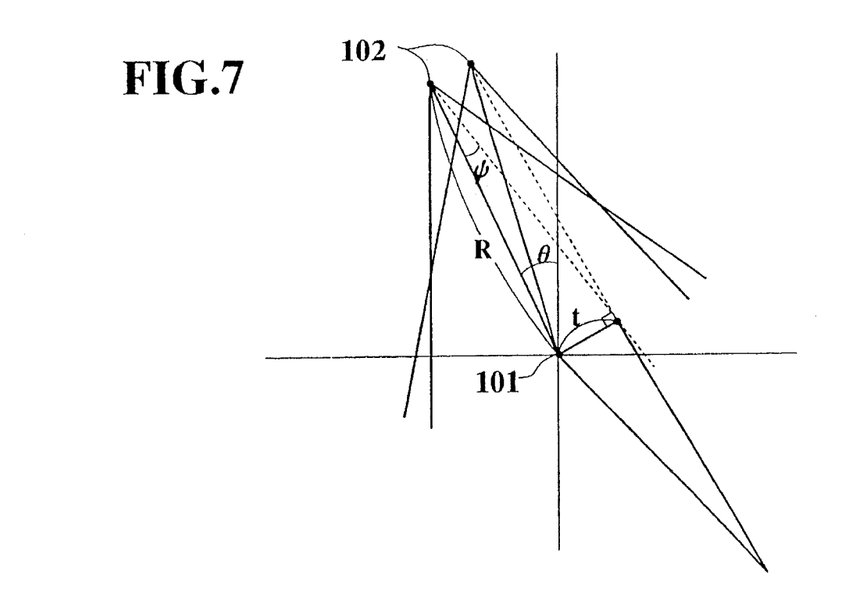
FIG. 7 is a schematic diagram for explaining a conventional fan-parallel data conversion.

In the above described conventional apparatus, the fan-parallel data conversion means that data corresponding to parallel beam data are picked up from the whole fan beam data and lacking parallel beam data are formed by an interpolation method. For instance, as shown in FIG. 7 wherein 101 and 102 denote a rotation center of a fan beam collimator and a focal point, respectively, a relation between fan beam data $X_F(\theta,\psi)$ and parallel beam data $X_P(\theta,t)$ is satisfied in the following formula.

$$X_P(\theta,t) = X_F\left(\theta - \sin^{-1}\frac{t}{R}, \sin^{-1}\frac{t}{R}\right)$$

or $$= X_F\left(\pi + \theta + \sin^{-1}\frac{t}{R}, -\sin^{-1}\frac{t}{R}\right)$$

That is, when there is unlimited fan beam data, parallel beam data can be obtained from the fan beam data by using this formula. In practice, however, the parallel beam data obtained from the conversion of the fan beam data does not always exactly correspond to the parallel beam data, and the parallel beam data is obtained by interpolation.

In the conventional apparatus using the fan-parallel data conversion algorithm, the fan-parallel data conversion cannot be carried out without all of the fan beam data. Further, since the number of readings when collecting of the collection data in the fan-parallel data conversion is large, it takes a long time to obtain the parallel beam data, and this is improper to the SPECT apparatus capable of collecting a plurality of slices of data at the same time. Further, since new data is stored in a memory to renew the old data in the preprocess (when the old data is required, they are copied), the data processing is complicated, and the data processing time is apt to be long. On the other hand, when the direct reconstruction algorithm is used, the calculation of the data processing is very complicated, and the conventional SPECT apparatus including the parallel beam data reconstruction system can not be used easily.

Further, in a conventional SPECT apparatus, a matrix size and a data collection angle pitch (hereinafter referred to as an angle) of a projection image (fan beam projection image) produced using the fan beam projection data are determined to the same values as those of parallel beam projection data obtained by the fan-parallel data conversion of the fan beam projection data. In the conventional apparatus, the maximum matrix size of the fan beam projection image is 128×128. However, in order to improve a resolving power for obtaining a superior image, a pixel size should be reduced. Hence, the matrix size is to be enlarged to one step larger size such as 256× 256.

However, when the matrix size of the fan beam projection image is enlarged to 256×256 in order to improve the resolving power, the data amount to be processed in the fan-parallel data conversion is very much increased, and a memory having a large memory size is required. Further, a processing speed is fairly reduced to, for example, approximately ¼.

SUMMARY OF THE INVENTION

Accordingly, it is an object of the present invention to provide a SPECT apparatus, free from the aforementioned defects and disadvantages of the prior art, which is capable of collecting fan beam data in a short time, carrying out a fan-parallel data conversion to obtain parallel beam data, and reconstructing an image from the parallel beam data.

It is another object of the present invention to provide a SPECT apparatus in view of the aforementioned defects and inconveniences of the prior art, which is capable of carrying out a fan-parallel data conversion without increasing data amount in the fan-parallel data conversion, deteriorating image information and reducing a processing speed.

In accordance with one aspect of the present invention, there is provided a SPECT apparatus for forming a radioisotope distribution tomographic image of an object, comprising detecting means for detecting fan beam shaped gamma ray emitted from a radioisotope given to the object to provide fan beam data, scanning means for causing relative rotation between the object and the detecting means, data collector means for collecting the fan beam data, data converter means for successively converting the fan beam data into parallel beam data during the relative rotation, and reconstructor means for reconstructing a tomographic image from the parallel beam data.

In accordance with another aspect of the present invention, there is provided a SPECT apparatus for forming a tomographic image, comprising detecting means for detecting fan beam shaped gamma ray emitted from a radioisotope given to an object to provide fan beam data having a first matrix size and a first angle, scanning means for causing relative rotation between the object and the detecting means, data converter means for converting the fan beam data into parallel beam data having a second matrix size different from the first matrix size and a second angle different from the first angle, and reconstructor means for reconstructing an image from the parallel beam data.

BRIEF DESCRIPTION OF THE DRAWINGS

The above and other objects, features and advantages of the present invention will more fully appear from the following description of the preferred embodiments with reference to the accompanying drawings, in which:

FIGS. 11a to 11c schematically show fan beam data and parallel beam data produced therefrom;

DESCRIPTION OF THE PREFERRED EMBODIMENTS

Figure 8:
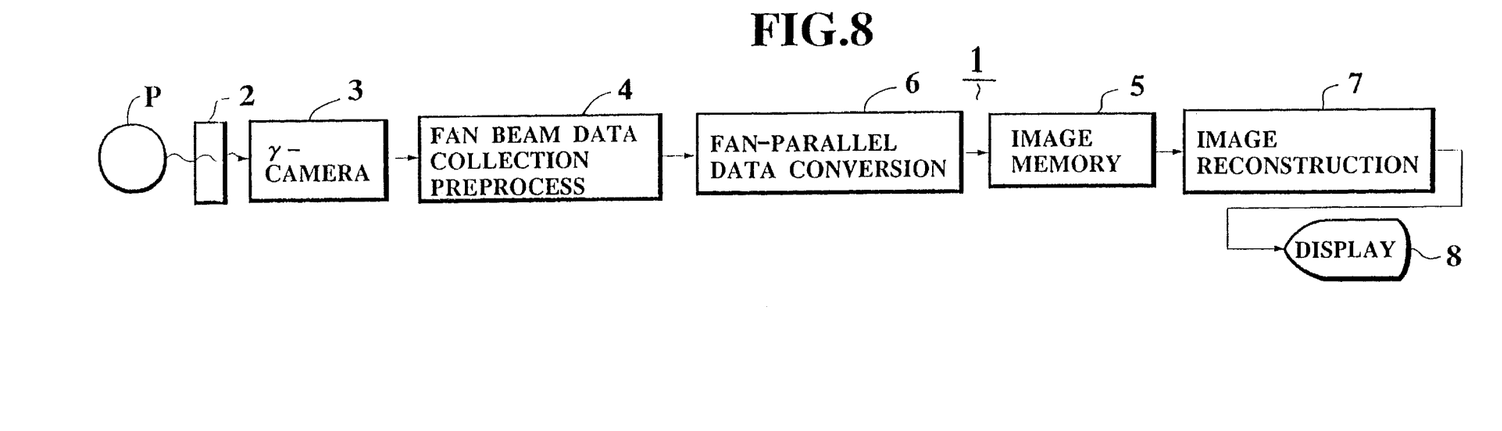
FIG. 8 is a schematic block diagram of a SPECT apparatus according to the present invention.

Referring now to the drawings, wherein like reference characters designate like or corresponding components throughout the several views and thus the repeated description can be omitted for brevity, there is shown in FIG. 8 a first embodiment of a SPECT (Single-Photon Emission Computed Tomography) apparatus 1 according to the present invention.

As shown in FIG. 8, in the SPECT apparatus 1, a gamma camera 3 detects gamma rays emitted by an RI (radioisotope) given to an object P through a fan beam collimator or collimators 2 to output fan beam data to a fan beam data collection preprocess means 4 for carrying out a preprocess of the fan beam data in order to improve quality of a picked up image. The preprocessed fan beam data is fed from the fan beam data collection preprocess means 4 to a fan-parallel data conversion means 6 for converting the fan beam data into parallel beam data to output the obtained parallel beam data to an image memory 5 for storing the parallel beam data therein. The parallel beam data read out of the image memory 5 are sent to an image reconstruction means 7 for reconstructing an image by using the parallel beam data to output TV image signal to a display for displaying a density distribution tomographic image of the RI in the object P.

When photographing the object P, the fan beam collimators 2 and the gamma camera 3 are rotated around the object P and detect the gamma rays from all directions (e.g. 360 degrees around the object). The operation of the fan beam collection preprocess means 4 and the fan-parallel data conversion means 6 will be described in detail as follows in connection with FIG. 9.

Figure 9:
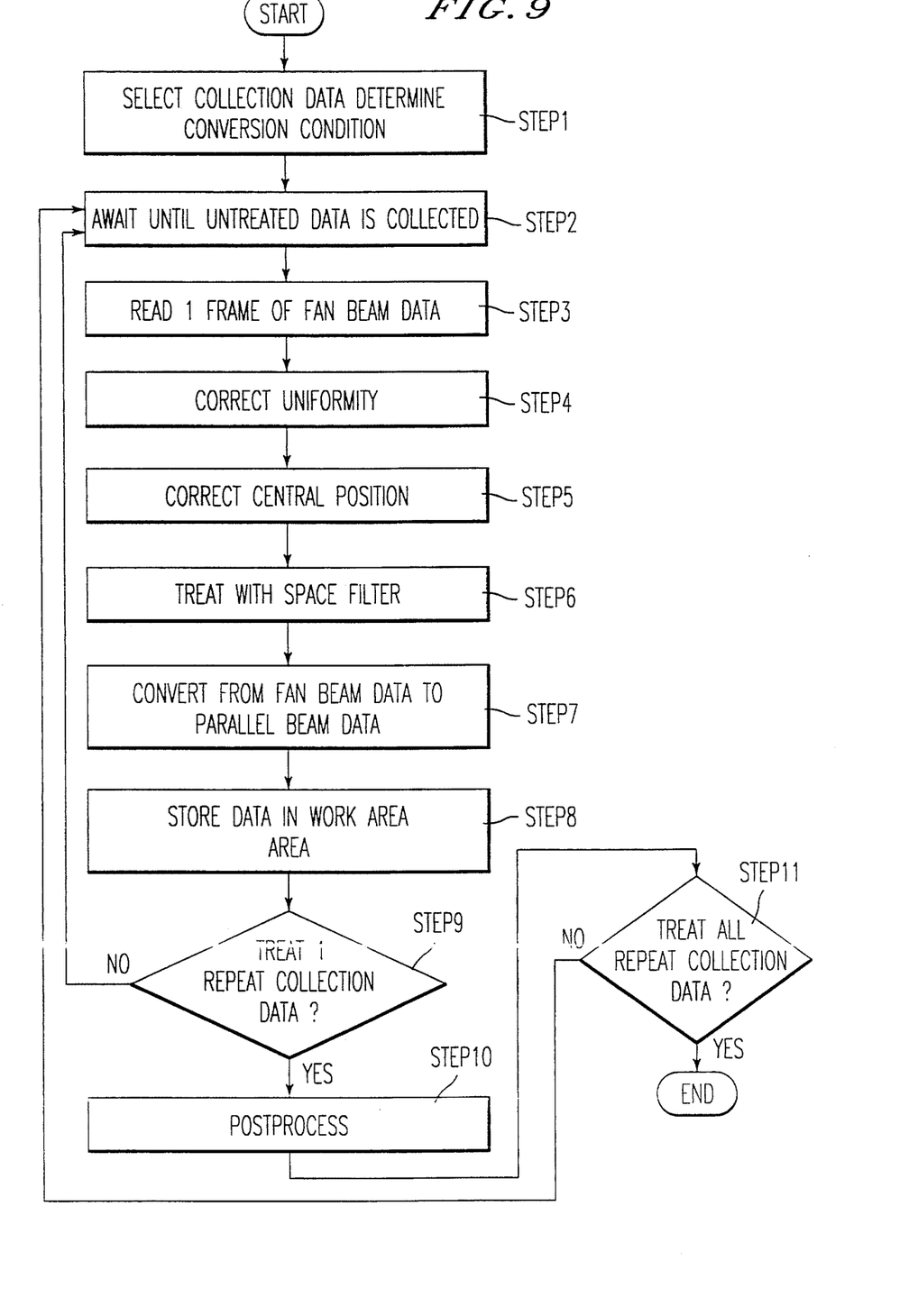
FIGS. 9 and 10 are flow charts for operating the SPECT apparatus shown in FIG. 8 according to the present invention.

As shown in FIG. 9, in step 1, collection data for obtaining a picked up image are selected and fan-parallel data conversion conditions are determined. After awaiting until unprocessed data are collected in step 2, one frame of the collected fan beam data is read out in step 3, and a preprocess such as a uniformity correction in step 4, a central position correction in step 5 and a space filter process in step 6 of the readout collection fan beam data is carried out.

That is, in the uniformity correction, planar image data of uniform surface line source is collected in advance by using the fan beam collimator 2, and a sensitivity component of the fan beam collimator 2 is removed from the planar image data to obtain uniformity variation data. Then, reciprocal numbers of the uniformity variation data are taken to form uniformity correction data. The uniformity correction data is multiplied with the collection data to remove an ununiform component of the gamma camera 3. In the central position correction, a discrepancy amount relative to the true rotation center of the visual field center of the gamma camera 3 is measured at every data collection angle to obtain a correction amount from the discrepancy amount, and the rotation center on the image is corrected to a proper position by shifting the collection data image by a correction amount portion. In the space filter process, a space filter for removing a noise component or components is multiplied with the collection data. The filter types and filter matrixes can be optionally selected.

After the above described preprocess, in step 7, the fan beam data is converted into the parallel beam data in the fan-parallel data conversion means 6. That is, in the SPECT apparatus, one projection of data collection time is long, and thus by utilizing the idle time of a CPU during the data collection operation, the collected fan beam data is successively converted into the parallel beam data. In the fan-parallel data conversion in this embodiment, parallel converted data is obtained from two frames of collection data, and the parallel beam data is formed from the parallel converted data and is then written in addresses corresponding to a conversion image in the image memory 5.

Figure 11:
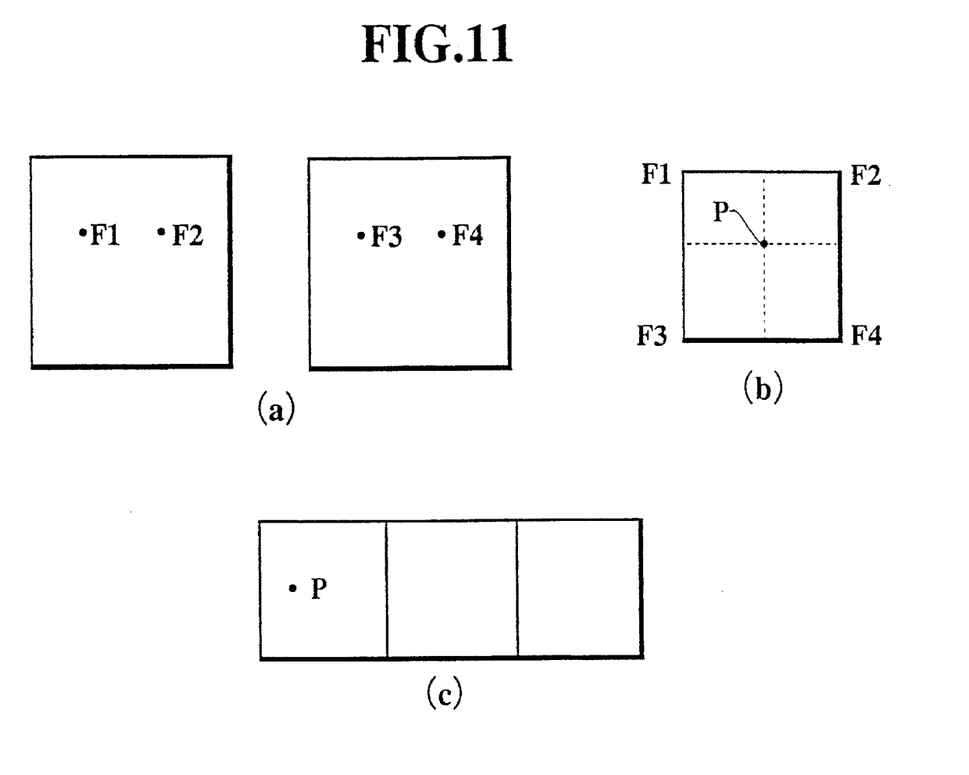
Figure 12:
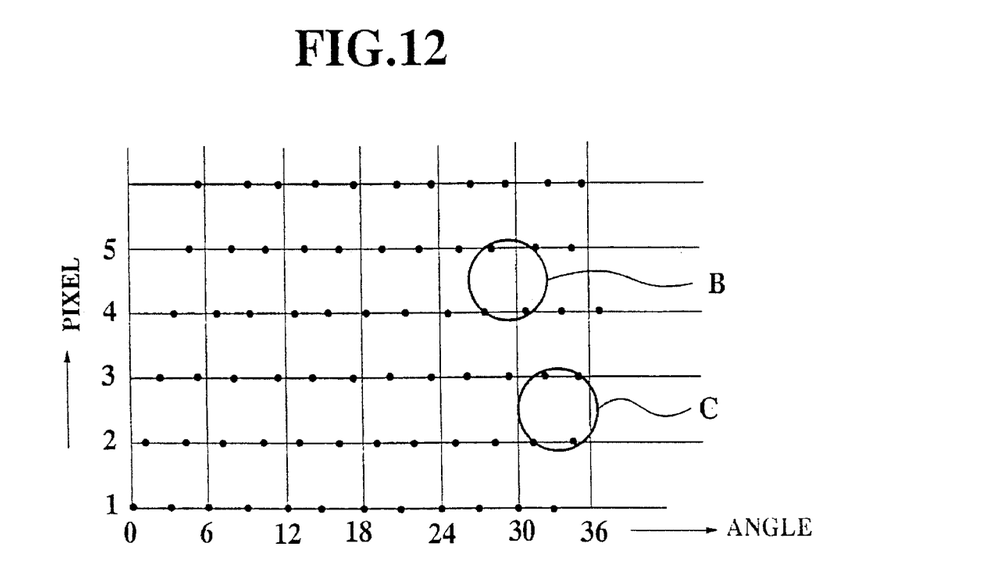
FIG. 12 is a schematic diagram showing the fan beam data represented by fan beam angle and pixel position of a camera.

For instance, in the fan-parallel data conversion, fan beam data F1 and another fan beam data F2 adjacent thereto for one collection beam angle and fan beam data F3 and another fan beam data F4 adjacent thereto for a next collection beam angle as shown in FIG. 11a are arranged in four points as shown in FIG. 11b, and the parallel beam data P as shown in FIG. 11c are formed from the fan beam data F1 to F4 shown in FIG. 11b by an interpolation. That is, the fan beam data are exhibited by the beam angle and the pixel position of the camera as shown in FIG. 12. In FIG. 12, in an area B, when there is parallel beam data (at lattice points), the parallel beam data is formed from the fan beam data (black dots) in the four points in the area B by the interpolation, and in an area C, when there is no parallel beam data, nothing is carried out.

In this data conversion process, the calculation is carried out for all pixels of the adjacent two frames of the fan beam data. According to this method, when two adjacent fan beam data exist, the fan-parallel data conversion can be partially performed, and the same process is carried out for the entire peripheral fan beam data to obtain all parallel beam data, thereby finishing the fan-parallel data conversion.

Figure 13:
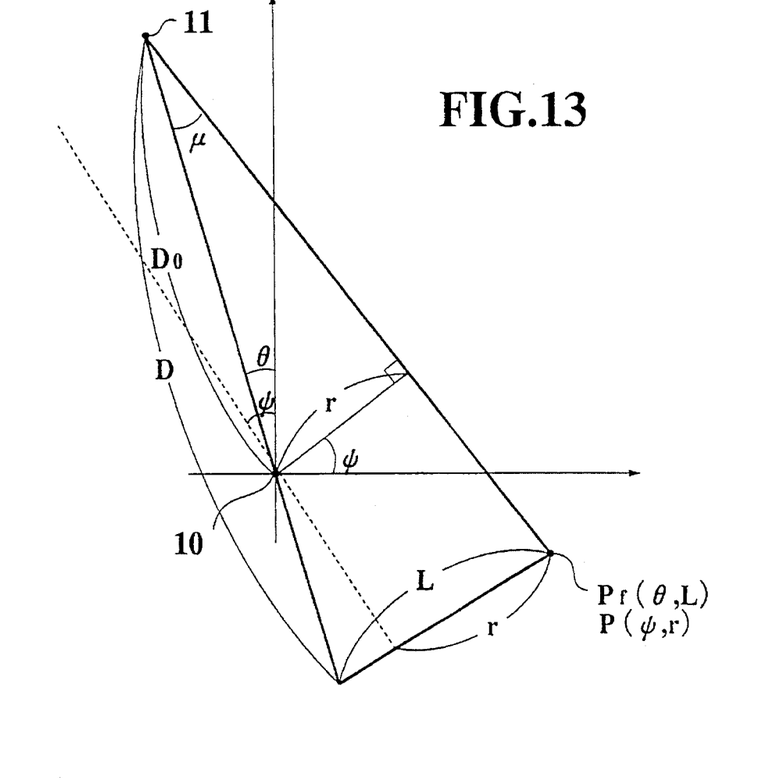
FIG. 13 is a schematic diagram for explaining a relation between the fan beam data and parallel beam data.

That is, in the fan-parallel data conversion means 6, when there exists another frame of collected fan beam data preprocessed right before one frame of fan beam data to be processed, the parallel beam data obtainable from these two frames of the fan beam data is checked to conduct the fan-parallel data conversion. Now, a method for converting from the fan beam data into the parallel beam data will be described as follows. As shown in FIG. 13, the parallel beam data $P(\psi,r)$ corresponding to the fan beam data $Pf(\theta,L)$ satisfy the following formulas, $$\tan \mu = L/D \quad \mu = \tan^{-1}(L/D) \quad \psi = \theta + \mu \quad (1)$$

$$r = D_o \cdot \sin \mu \quad (2)$$

wherein $\mu$ is an opening angle of fan beam, $D_o$ is a distance between a focal point of the fan beam and a rotation center 10, and D is a distance between the focal point of the fan beam and a surface (detection surface) of a scintillator of a gamma camera 3. The parallel beam data corresponding to the fan beam data can be obtained according to the above two formulas (1) and (2).

Figure 14:
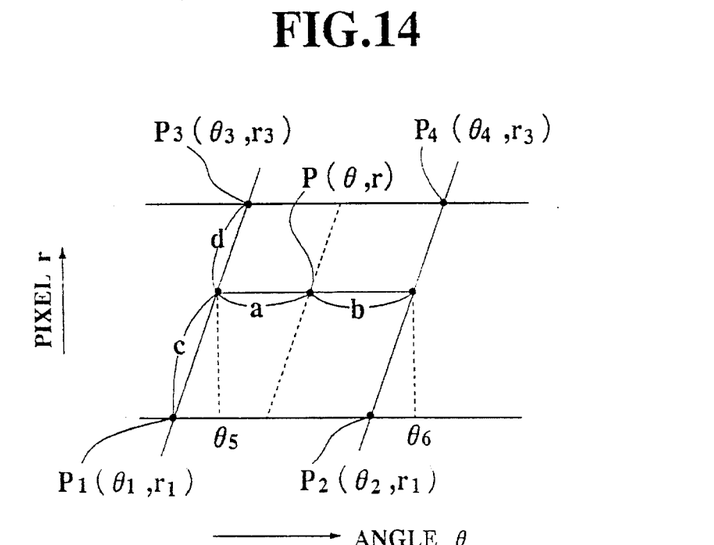
FIGS. 14 to 16 are schematic diagrams for explaining fan-parallel data conversion in the SPECT apparatus shown in FIG. 8.

FIG. 14 shows fan beam data determined by a fan beam angle $\theta$ and a pixel r. It is checked whether or not parallel beam data $P(\theta,r)$ exists among four fan beam data $P_1(\theta_1,r_1)$, $P_2(\theta_2,r_2)$, $P_3(\theta_3,r_3)$ and $P_4(\theta_4,r_4)$ arranged in mutual adjacent positions. Firstly, it is checked whether or not r satisfying the following formula exists.

$$r_1 \leq r < r_3 \quad (3)$$

When a value of r exists, angles $\theta_5$ and $\theta_6$ shown in FIG. 14 are obtained by using the following formulas.

$$\frac{\theta_5 - \theta_1}{r - r_1} = \frac{\theta_3 - \theta_1}{r_3 - r_1}$$

Therefore, $$\theta_5 = \frac{r - r_1}{r_3 - r_1}(\theta_3 - \theta_1) + \theta_1$$

$$\theta_6 = \theta_5 + (\theta_2 - \theta_1)$$

$$= \frac{r - r_1}{r_3 - r_1}(\theta_3 - \theta_1) + \theta_2$$

Then, it is checked whether or not $\theta$ satisfying the following formula exists.

$$\theta_5 \leq \theta < \theta_6 \quad (4)$$

when the r and $\theta$ satisfying the respective formulas (3) and (4) exist, the parallel beam data $P(\theta,r)$ exists. However, a plurality of parallel beam data may exist depending on conditions. In such a case, all parallel beam data are obtained. When the parallel beam data exists, the parallel beam data is formed from the four fan beam data arranged in its surrounding four points.

In this case, weights or factors to be multiplied to the four data are calculated. In FIG. 14, for instance, the weights a', b', c' and d' in proportion to lengths a, b, c and d will be determined as follows.

These weights a', b', c' and d' satisfy the following standardizing conditions.

$$a'+b'=1 \text{ and } c'+d'=1$$

In this case, since $c':d'=c:d=r-r_1:r_3-r$, the weights a', b', c' and d' are obtained according to the following formulas, $$a' = \frac{\theta - \theta_5}{\theta_6 - \theta_5}, \quad b' = \frac{\theta_6 - \theta}{\theta_6 - \theta_5}$$

$$c' = \frac{r - r_1}{r_3 - r_1}, \quad d' = \frac{r_3 - r}{r_3 - r_1}$$

wherein $\theta_6 - \theta_5$ is a sampling angle. Hence, the parallel beam data can be obtained from the following formula.

$$P(\theta,r) = b' \cdot d' \cdot P_1 + a' \cdot d' \cdot P_2 + b' \cdot c' \cdot P_3 + a' \cdot c' \cdot P_4$$

Figure 15:
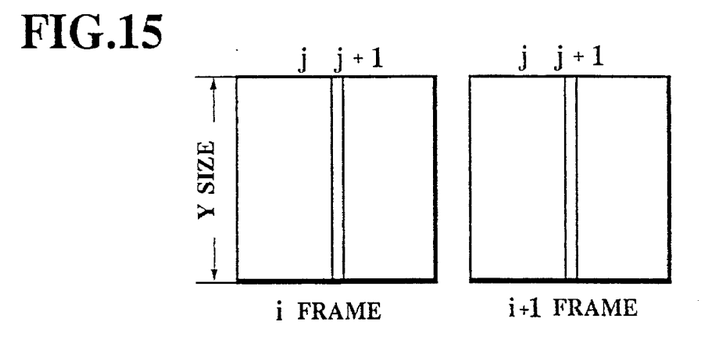
Figure 16:
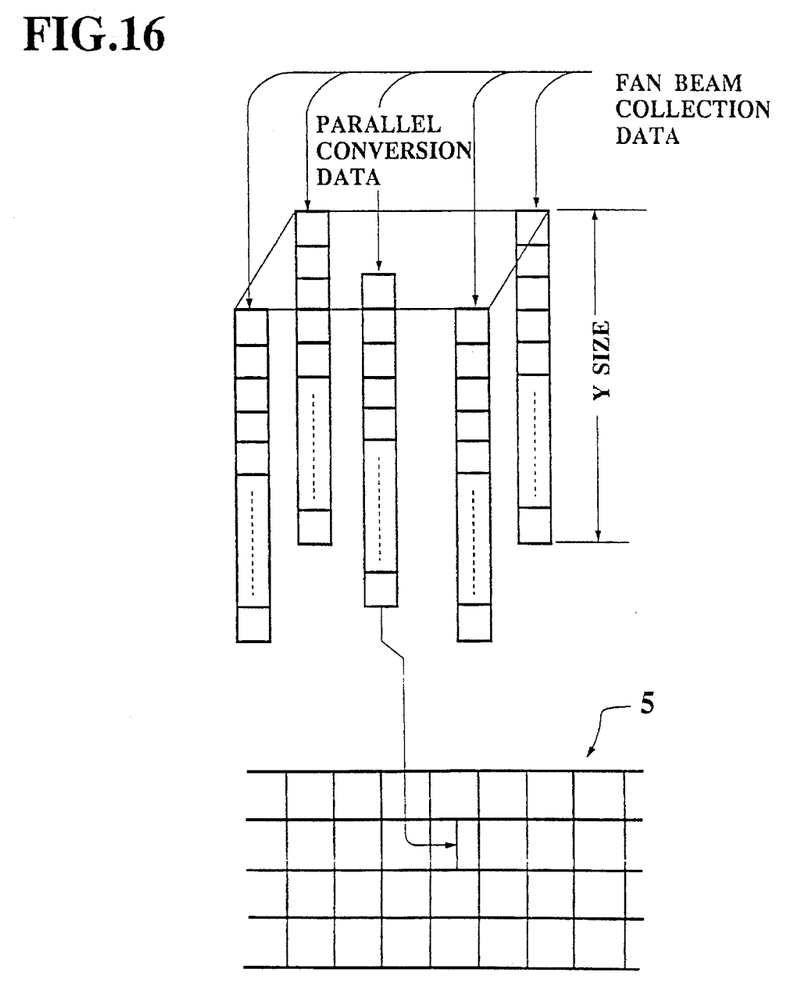

In the above described method, the position of the parallel beam data in the x-direction can be obtained, and since data is positioned in parallel in the y-direction (slice direction), when the position of the parallel beam data in the x-direction is determined, the position of the parallel beam data in the y-direction is automatically determined in the same position as that of the fan beam data. Accordingly, as shown in FIG. 15, the data of the pixels j and j+1 in the x-direction is picked up with its image size (Y size) portion in the y-direction from the two continuous frames i and i+1 of fan beam data to form a plurality of slice portions of fan-parallel conversion data at one time. The resulted parallel beam data are written in the work area of the image memory 5 in step 8, as shown in FIG. 16. Thus, a plurality of slices of fan-parallel data conversion can be readily carried out.

The above described steps are repeated until one repeat of collection data is processed to carry out the fan-parallel data conversion of one repeat of collection data in step 9, and then a postprocess of the parallel beam data is carried out In step 10. That is, after the fan-parallel data conversion, when the image sizes in the x- and y-directions are different, the image sizes in the x- and y-directions are corrected to the same sizes. The above described steps are repeated until all repeats of collection data are processed in step 11, thereby finishing the operation.

Figure 10:
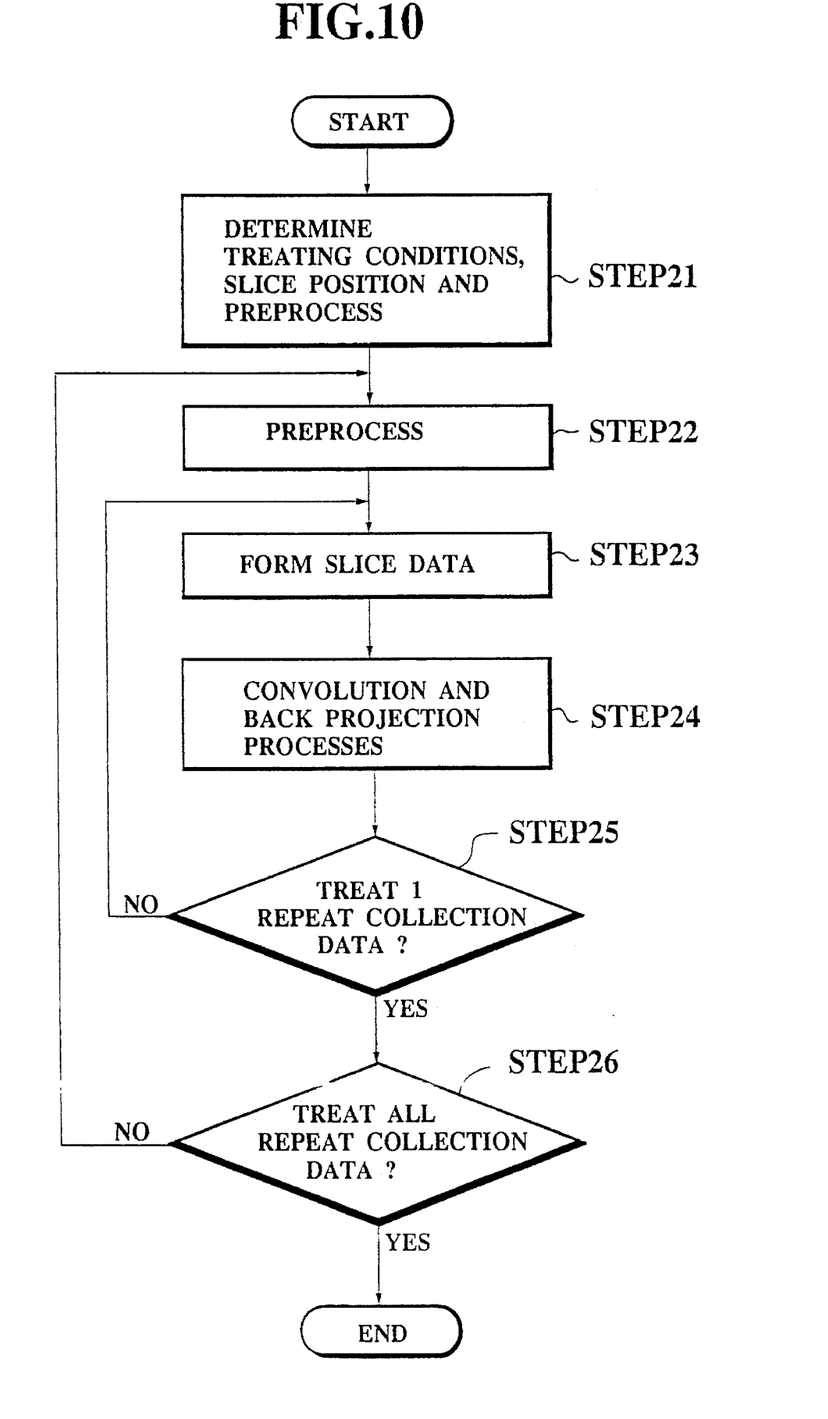

As shown in FIG. 10, the image reconstruction is carried out by using the parallel beam data stored in the image memory 5 in the image reconstruction means 7 as follows. The processing conditions, the slice positions and the preprocess conditions are determined in step 21, and the preprocess for the image reconstruction is performed in step 22. The data for obtaining the slice image are formed in step 23, and the convolution and back projection process to the obtained data is carried out to reconstruct the image in step 24. The steps 23 and 24 are repeated until one repeat of data is processed in step 25. Then, the steps 22 to 25 are repeated until all repeats of data are processed in step 26. The TV signals representing the obtained reconstruction image are fed from the image reconstruction means 7 to the display 8, and the display 8 displays a slice image exhibiting a density distribution of the RI in the object P.

As described above, according to the present invention, the fan beam data collection, the preprocess and the fan-parallel data conversion can be readily carried out in a simple manner in a short time, and the preprocess for improving the image quality can be readily applied to the fan beam data without writing it in the data. Further, since the fan beam data is read in only once when the fan-parallel data conversion is performed, a variety of preprocesses can be added or the preprocess conditions can be readily changed when the data is read in.

Relating to a parallel beam SPECT apparatus, a fan beam data collector is provided, and parallel beam collimators are replaced by fan beam collimators to realize a fan beam SPECT apparatus in a simple manner. To be exact, the information for the used fan beam collimator or collimators is added to the fan beam data, but it is unnecessary to largely change the construction of the apparatus itself. That is, by providing the fan beam data collection preprocess means 4 and the fan-parallel data conversion means 6, the conventional SPECT apparatus including a parallel beam data reconstruction system can be reconstructed to a SPECT apparatus according to the present invention in a simple manner by using the original functions as it is. Further, in this case, the particular process of the fan beam SPECT apparatus is added as the functions of the fan beam data collection preprocess means 4 and the fan-parallel data conversion means 5 without affecting the rest of the system.

Further, since fan-parallel data conversion software includes a suitable fan-parallel data conversion algorithm for the SPECT data collection in this apparatus, the structure of the system is simple. Also, the conventional parallel beam data SPECT apparatus can be used by reconstructing as described above, i.e., adding the fan-parallel data conversion operation, and the operation change is small and is therefore not a burden on the operator of the system.

In the fan beam data collection preprocess means 4 and the fan-parallel data conversion means 6, a software package for carrying out the above described processes in a computer software form can be included.

Figure 17:
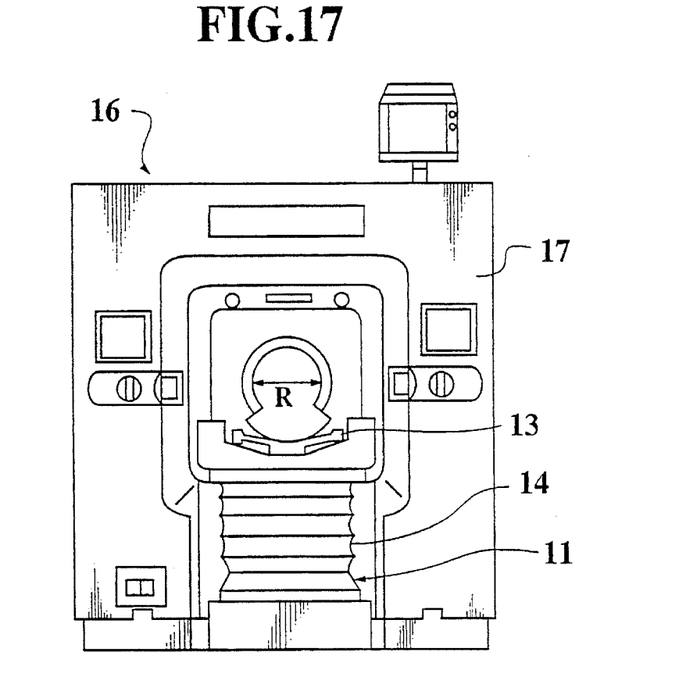
FIG. 17 is another SPECT apparatus according to the present invention.
Figure 18:
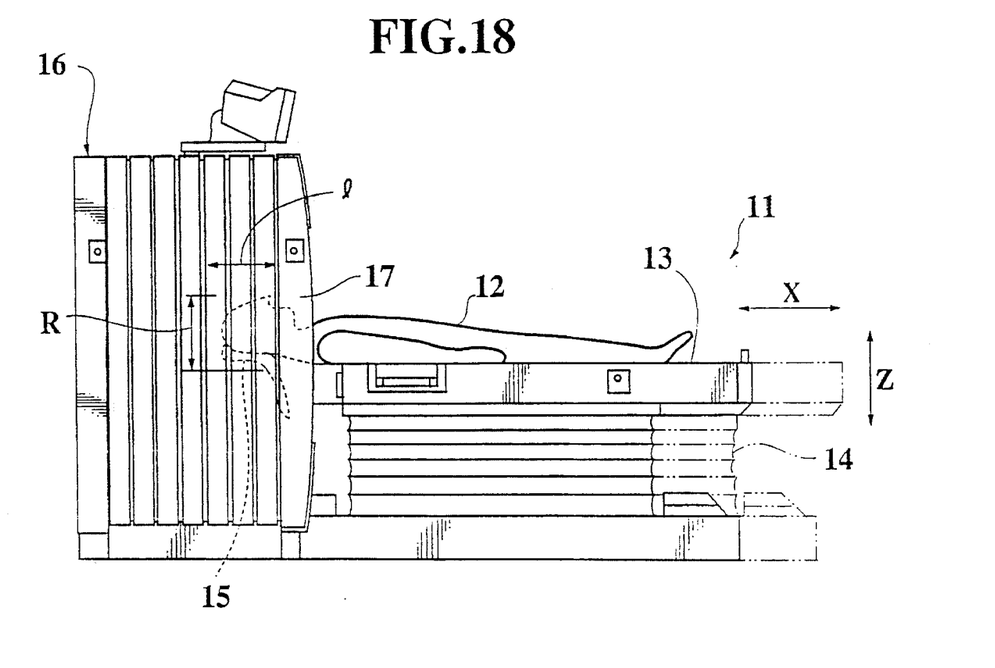
FIG. 18 is a side view of FIG. 17.

In FIGS. 17 and 18, there is shown another embodiment of a SPECT apparatus according to the present invention, and particularly a SPECT apparatus for obtaining a tomographic image of a head portion of an object such as a human being.

Figure 19:
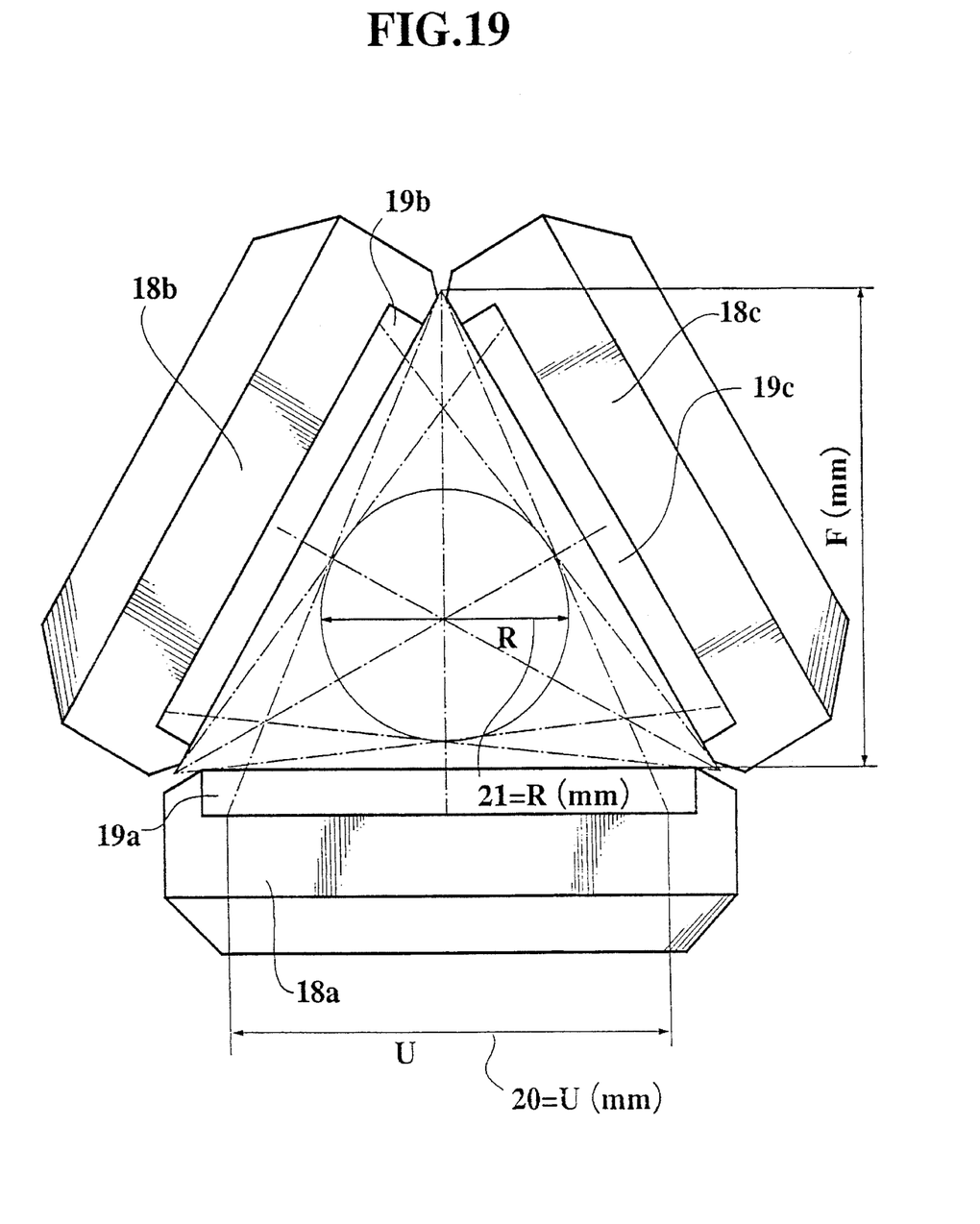
FIG. 19 is a front view showing gamma cameras used in the SPECT apparatus shown in FIG. 17.

As shown in FIGS. 17 and 18, a bed section 11 includes a support plate 13 for supporting an object 12 such as a patient or the like thereon, and a height control mechanism 14 for adjusting the height of the support plate 13 in the vertical direction Z. The support plate 13 is also adapted to be movable in the X direction so as to move into or from a frame section 16. The bed section 11 is formed with a head rest 15 for fixing a head portion of the object 12. The RI is administered to the object 12 laid on the support plate 13. The frame section 16 includes a dome 17 for guiding the object 12 supported on the support plate 13, three Anger type gamma cameras 18a, 18b and 18c arranged in a triangular form at 120 degree in the peripheral portion of the dome 17, as shown in FIG. 19. The gamma cameras 18a, 18b and 18c are rotated around the object 12.

Figure 20:
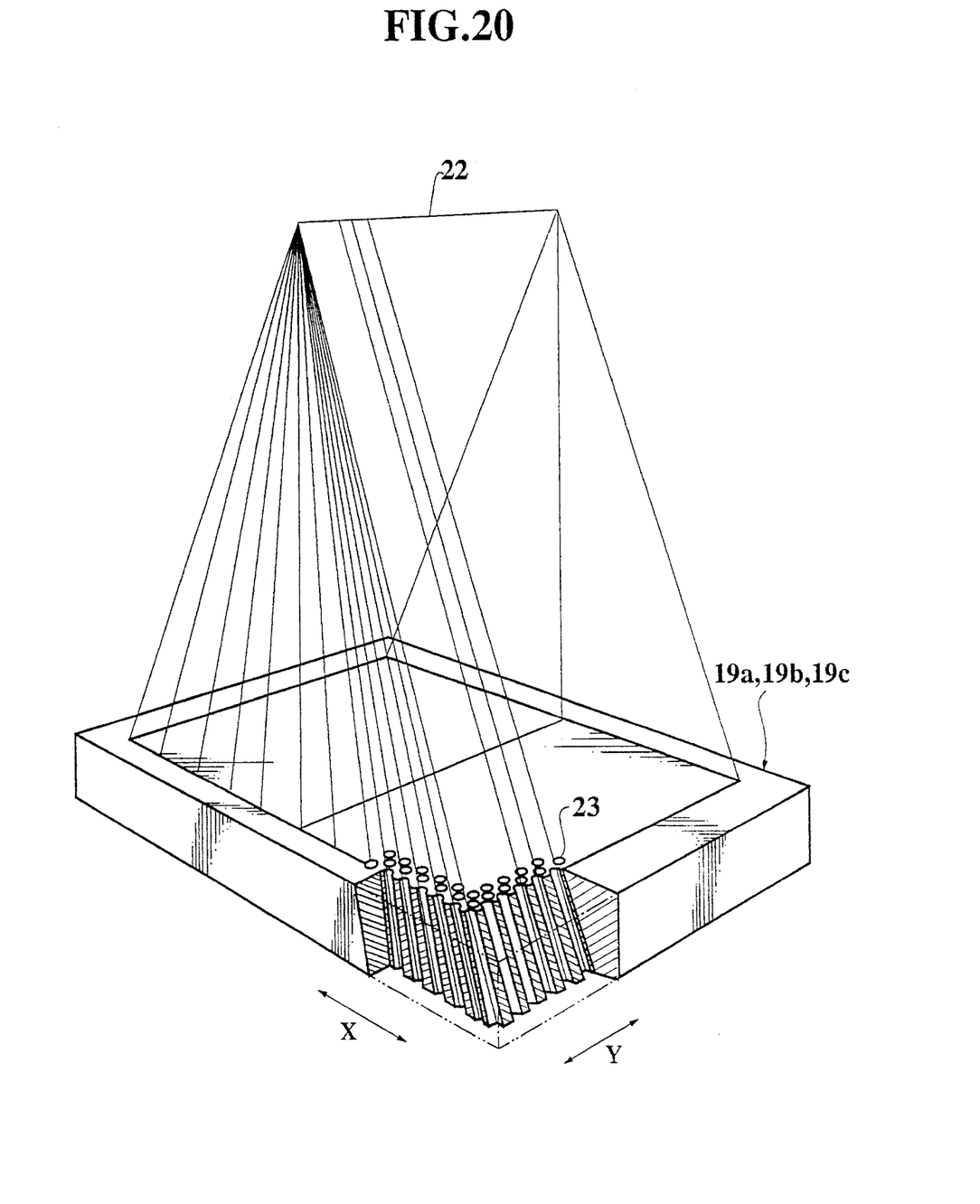
FIG. 20 is a perspective view of a fan beam collimator shown in FIG. 19.

In the dome 17, a space defined by a diameter R and a length l is an effective visual field for detecting the gamma rays. A visual field 20 of the gamma camera has a dimension U mm, and the diameter N represents a dimension R mm of the effective visual field. The gamma camera 18a, 18b or 18c is provided with a respective fan beam collimator 19a, 19b or 19c, as shown in FIG. 20. Each fan beam collimator 19a, 19b or 19c is formed with guide holes 23 which are aligned in one horizontal direction X along the object 12 in parallel with another horizontal direction Y perpendicular to the direction X so as to focus to a focal line 22.

In this embodiment, the three gamma cameras 18a, 18b and 18c are rotated 120 degrees around the object 12, and the gamma rays emitted by the RI given in the object 12 are detected by the fan beam collimators 19a, 19b and 19c through their guide holes 23 to collect fan beam projection data for a fan beam projection image. The fan beam projection data is converted into parallel beam projection data for a parallel beam projection image, and the parallel beam projection data is reconstructed to obtain a tomographic image (SPECT image).

Figure 21:
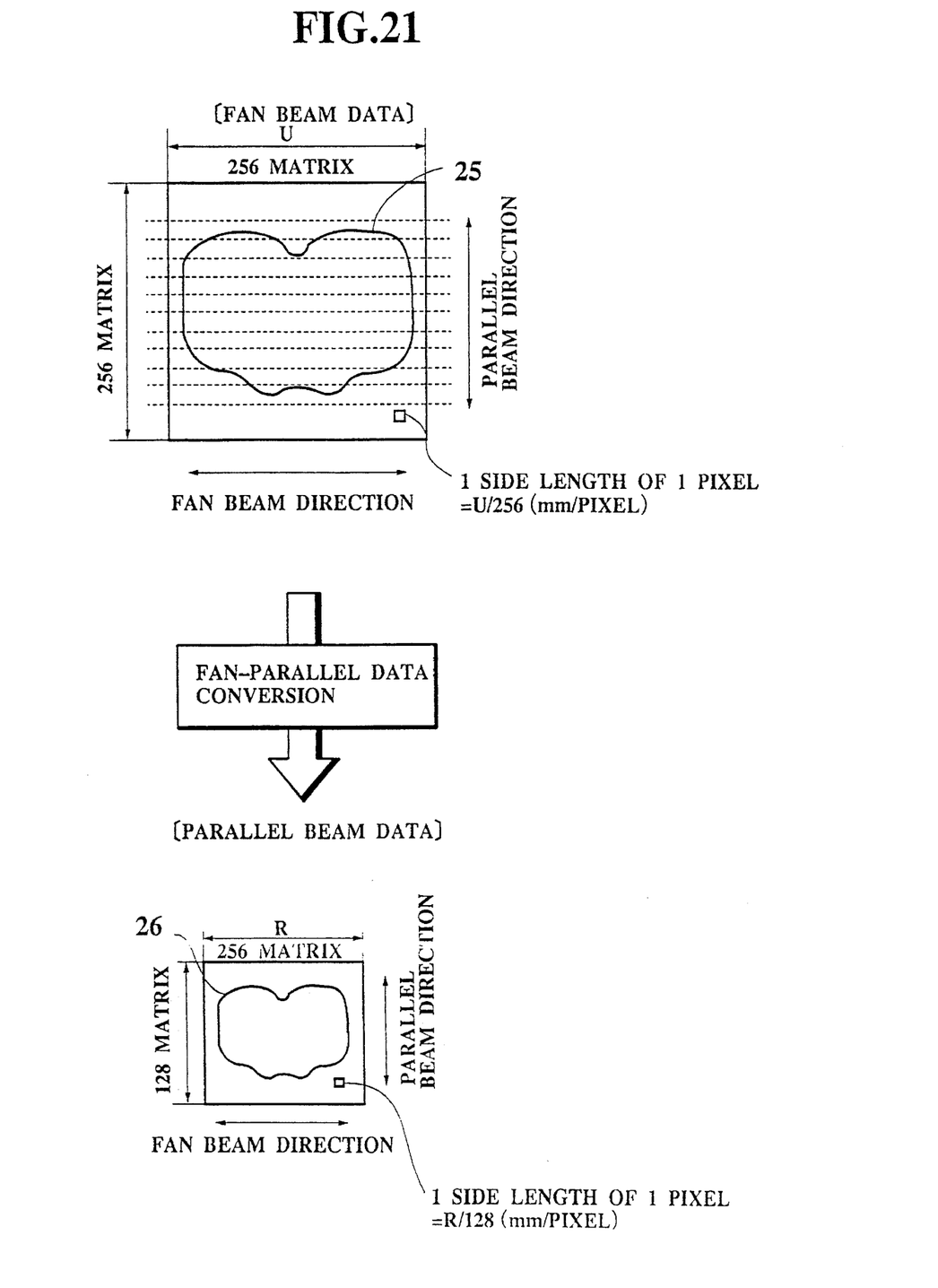
FIG. 21 is a schematic view showing a fan-parallel data conversion carried out in the apparatus shown in FIG. 17.

In this case, as shown in FIG. 21, by using the visual field dimension U and the effective visual field dimension R of the gamma camera, fan beam projection data for a fan beam projection image 25 having a matrix size of 256×256 in fan and parallel beam directions are collected by using the gamma cameras 18a, 18b and 18c which are rotated 120 degree around the object 12. One side length of one pixel is U/256 mm. Then, the fan beam projection data is converted into parallel beam projection data for a parallel beam projection image 26 having a matrix size of 128×128 in the fan and parallel beam directions by carrying out a conversion only in the fan beam direction. One side length of one pixel is R/128 mm. Then, the obtained parallel beam projection data is reconstructed to obtain a tomographic image. In this instance, the focal distance F is determined be, for example, 400 mm. In this embodiment, the fan-parallel data conversion can be carried out as described above without increasing the amount of data. As shown in FIG. 21, the fan beam projection data is two-dimensional data and is parallel data in the parallel beam direction. Hence, the fan-parallel data conversion of the fan beam projection data is carried out only in the fan beam direction. At the same time, the fan beam projection data is changed in its length at a ratio of U/256:R/128 and is converted into the parallel data aligned in common in the parallel beam direction.

Figure 22:
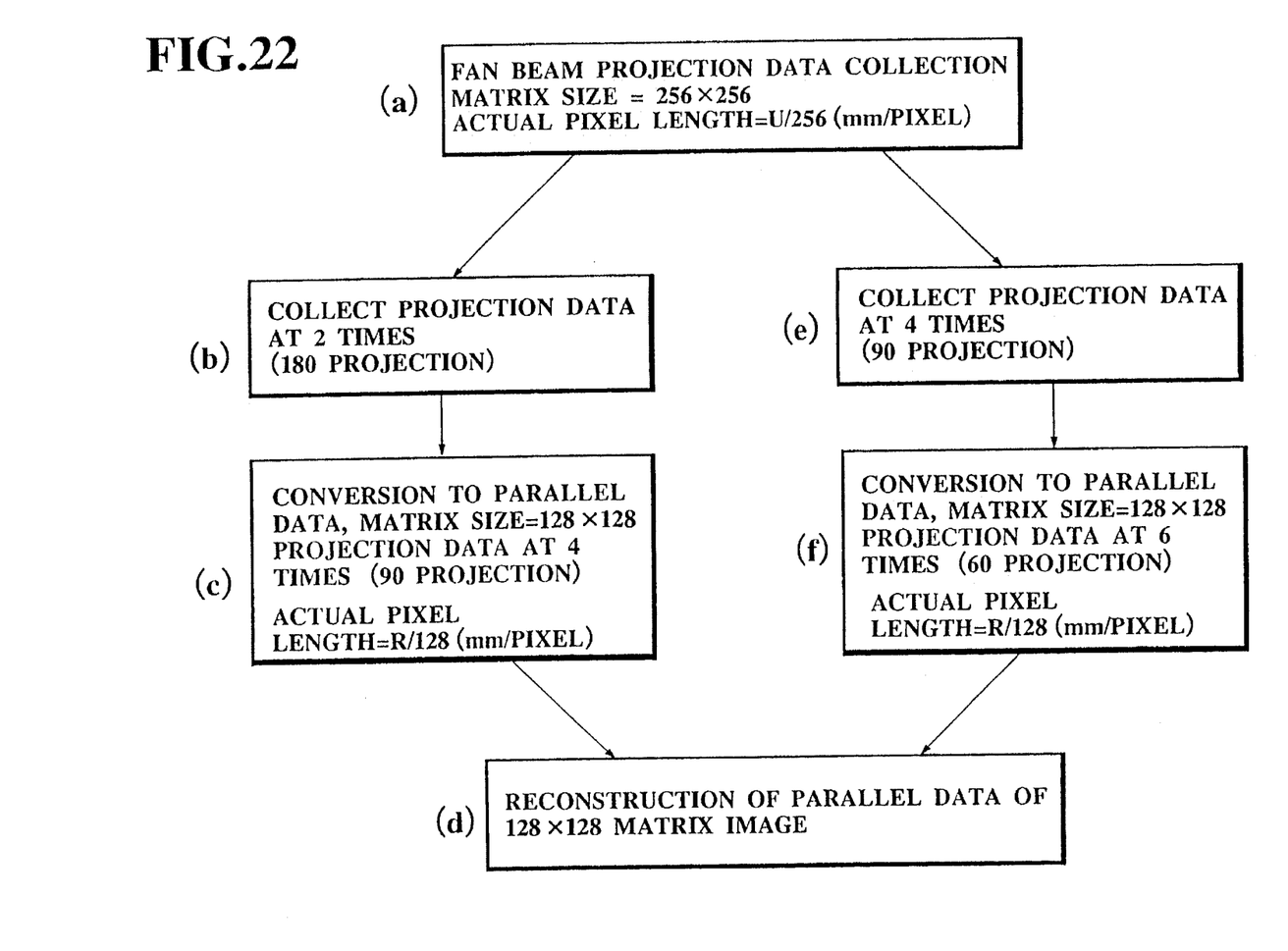
FIG. 22 is a flow chart explaining the fan-parallel data conversions In the apparatus shown in FIG. 17.

The operation of the data collection in the apparatus shown in FIGS. 17 and 18 will be described in detail in connection with FIG. 22.

Firstly, a process A is described. That is, fan beam projection data having a matrix size of 256×256 is collected in step (a), and this collection condition is a collection of the fan beam projection data from 360 degree at 2 times (or data collection angle pitch (hereinafter referred to as angle or angles in short)) (180 projection) in step (b). A fan-parallel data conversion of the fan beam projection data is carried out to collect parallel beam projection data having a matrix size of 128×128 at 4 times or angles (90 projection) in step (c). Then, the reconstruction of the parallel beam projection data of the matrix size of 128×128 is carried out to obtain a tomographic image in step (d). In this instance, a relation of U/256:R/128 is kept constant in all steps.

Next, a process B is described. That is, fan beam projection data having a matrix size of 256×256 is collected in step (a), and this collection condition is a collection of the fan beam projection data from 360 degrees at 4 times or angles (90 projection) in step (e). A fan-parallel data conversion of the fan beam projection data is carried out to collect parallel beam projection data having a matrix size of 128×128 at 6 times or angles (60 projection) in step (f). Then, the reconstruction of the parallel beam projection data of the matrix size of 128× 128 is carried out to obtain a tomographic image in step (d). In this instance, a relation of U/256:R/128 is kept constant in all steps.

In this embodiment, as described above, the fan-parallel data conversion of the fan beam projection data into the parallel beam projection data can be carried out without deteriorating image information and increasing the amount of data.

That is, when one example of information of a matrix size of 256×256 in a depth direction is set to 12 bits, the collection at 2 times or angles of 180 projection of the fan beam projection data requires approximately 20 MB data capacity. However, in this embodiment, in the process A, by reducing the matrix size to 128×128, the data capacity is reduced to ¼, and in addition, by the data collection at 4 times or angles of 90 projection of the fan beam projection data conversion into the parallel beam projection data, the data capacity is further reduced to ½. Hence, the data capacity can be totally reduced to ⅛.

Further, in this embodiment, in the process B, by the data collection at 6 times or angles of 60 projection of the fan beam projection data conversion into the parallel beam projection data, the data capacity can be further reduced. Hence, in this embodiment, a large capacity of memory is not required to and therefore, the cost of the system can be reduced. Further, since the data capacity is not extremely increased, the reduction of the processing speed can be effectively prevented. Also, since the fan-parallel data conversion is carried out without deteriorating the image quality such as resolving power, artifact and the like, the diagnostic ability is not reduced.

Although the present invention has been described in its preferred embodiments with reference to the accompanying drawings, it It readily understood that the present invention is not restricted to the preferred embodiments and that various changes and modifications can be made by those skilled in the art without departing from the spirit and scope of the present invention.

What is claimed is:

1. A SPECT apparatus, comprising:

at least one gamma camera having a collimator for detecting fan beams of gamma rays having a focal point and for generating fan beam data samples from detected pixels;

scanning means for rotatably supporting said at least one gamma camera around a center of rotation to detect gamma rays emitted from an object located at the center of rotation at prescribed angles in a plane of rotation;

fan beam data collection means, connected to said at least one gamma camera, for successively collecting the fan beam data samples generated by said at least one gamma camera at each of said prescribed angles;

fan-parallel data conversion means, connected to said fan beam data collection means, for successively performing calculations on and converting said collected fan beam data samples to parallel beam data repeatedly each time after the completion of the collection of each of said fan beam data samples by said fan beam data collection means as said samples are collected at each of said prescribed angles;

image memory means connected to said fan-parallel data conversion means, for storing the parallel beam data which corresponds to the fan beam data samples obtained by said at least one gamma camera; and image reconstruction means, connected to said image memory means, for reconstructing a tomographic image from said parallel beam data wherein the number of pixels in the tomographic image is less than the number of detected pixels of said gamma camera.

2. The SPECT apparatus as claimed in claim 1, wherein said fan-parallel data conversion mean comprises:

means for interpolating, which interpolates data points between multiple fan beam data samples of said collected fan beam data samples.

3. The SPECT apparatus as claimed in claim 1 wherein said at least one gamma camera comprises one of three identical gamma cameras surrounding the object at equal angles from each other.

4. A SPECT apparatus, comprising:

at least one gamma camera having a collimator for detecting fan beams of gamma rays having a focal point and for generating fan beam data samples from detected pixels;

scanning means for rotatably supporting said at least one gamma camera around a center of rotation to detect gamma rays emitted from an object located at the center of rotation at prescribed angles in a plane of rotation;

fan beam data collection means, connected to said at least one gamma camera, for collecting the fan beam data samples which are generated by said at least one gamma camera at said prescribed angles and represent respective fan beam projections;

fan-parallel data conversion means, connected to said fan beam data collection means, for performing calculations on and converting said collected fan beam data samples to corresponding parallel beam data representing parallel beam projections;

memory means, connected to said fan-parallel data conversion means, for storing said parallel beam data; and image reconstruction means, connected to said memory means, for reconstructing a tomographic image from said parallel beam data, wherein said prescribed angles are different from each other by 2 degrees and further wherein said fan beam data represents a plurality of fan beam projections and said parallel beam data represent a plurality of parallel beam projections and wherein the number of pixels in the tomographic image is less than the number of detected pixels of said gamma camera.

5. The SPECT apparatus as claimed in claim 4, wherein said gamma camera collects said fan beam data with a resolution of 256×256 pixels and said tomographic image comprises 128×128 pixels.

6. A SPECT apparatus, comprising:

at least one gamma camera having a collimator for detecting fan beams of gamma rays having a focal point and for generating fan beam data samples from detected pixels;

scanning means for rotatably supporting said at least one gamma camera around a center of rotation to detect gamma rays emitted from an object located at the center of rotation at prescribed angles in a plane of rotation;

fan beam data collection means, connected to said at least one gamma camera, for collecting the fan beam data samples which are generated by said at least one gamma camera at said prescribed angles and represent respective fan beam projections;

fan-parallel data conversion means, connected to said fan beam data collection means, for performing calculations on and converting said collected fan beam data samples to corresponding parallel beam data representing parallel beam projections;

memory means, connected to said fan-parallel data conversion means, for storing said parallel beam data; and image reconstruction means, connected to said memory means, for reconstructing a tomographic image from said parallel beam data, wherein said prescribed angles are different from each other by 4 degrees and further wherein said fan beam data represents a plurality of fan beam projections and wherein the number of pixels in the tomographic image is less than the number of pixels detected of said gamma camera.

7. The SPECT apparatus as claimed in claim 6, wherein said gamma camera collects said fan beam data with a resolution of 256×256 pixels and said tomographic image comprises 128×128 pixels.

8. A method of generating a tomographic image in a SPECT apparatus, comprising the steps of:

obtaining first fan beam data of an object using a gamma ray detector having a collimator for detecting fan beams wherein the number of pixels in the tomographic image is less than the number of pixels detected of said gamma camera;

obtaining second fan beam data of the object using the gamma ray detector;

converting said first and second fan beam data to parallel beam data;

generating from said first and second fan beam data a set of first parallel beam data;

obtaining a third fan beam data of the object by using the gamma ray detector at a same time as said step of generating said first parallel beam data is being performed;

generating from said third fan beam data and at least one of said first and second fan beam data second parallel beam data; and generating from said first and second parallel beam data a tomographic image.

9. An apparatus for generating a tomographic image, comprising:

a gamma detector having a fan beam collimator for detecting given images having a number of pixels;

means for obtaining first fan beam data of an object using said gamma detector;

means for generating first parallel beam data in response to said first and second fan beam data;

means for obtaining third fan beam data of the object and for activating said gamma ray detector at the same time as said means for generating said first parallel beam data is generating said first parallel beam data;

means for generating and converting second parallel beam data responsive to said third fan beam data and responsive to at least one of said first and second fan beam data;

means for generating a tomographic image in response to said first and second parallel beam data wherein the number of pixels in the tomographic image is less than the number of detected pixels of said gamma camera.

10. A SPECT apparatus comprising:

at least one gamma camera provided with a collimator for detecting fan beams of gamma rays having a focal point and wherein there is a number of pixels in the image, scanning means for supporting said gamma camera and a patient to allow relative rotation around a center of rotation in order to detect gamma rays emitted from said patient at prescribed angles in the plane of the rotation, fan beam data collection means, connected to said at least one gamma camera, for collecting fan beam data samples which are transmitted from said at least one gamma camera at said prescribed angles and represents respective fan beam projections;

fan-parallel data conversion means, connected to said image memory and said at least one gamma camera, for carrying, out fan-parallel data conversion;

image memory for storing fan-parallel data generated by said fan-parallel data converting means;

image reconstruction means, connected to said image memory, for reconstructing a tomographic image from said parallel beam data samples, wherein said fan-parallel data conversion is carried out, at each time that one sample of said fan beam data samples corresponding to one of said prescribed angles is transmitted from said at least one gamma camera to said fan-parallel data conversion means through said fan beam data collection means, using said image memory as a work area in which an intermediate result of said fan-parallel data conversion is readily saved until all the parallel data is formed in said image memory and wherein the number of pixels in the tomographic image is less than the number of detected pixels of said gamma camera.

* * * * *